(12) United States Patent
Shah et al.

(10) Patent No.: US 12,192,402 B2
(45) Date of Patent: Jan. 7, 2025

(54) CUSTOMER DISTRESS ASSISTANCE

(71) Applicant: Capital One Services, LLC, McLean, VA (US)

(72) Inventors: Salik Shah, Washington, DC (US); Jennifer Kwok, Brooklyn, NY (US); Abhay Donthi, Arlington, VA (US); Dwij Trivedi, Oakton, VA (US); Leeyat Bracha Tessler, Arlington, VA (US)

(73) Assignee: Capital One Services, LLC, McLean, VA (US)

( * ) Notice: Subject to any disclaimer, the term of this patent is extended or adjusted under 35 U.S.C. 154(b) by 257 days.

(21) Appl. No.: 17/869,292

(22) Filed: Jul. 20, 2022

(65) Prior Publication Data

US 2024/0031475 A1    Jan. 25, 2024

(51) Int. Cl.
H04M 3/22 (2006.01)
A61B 5/0205 (2006.01)

(52) U.S. Cl.
CPC ......... H04M 3/2281 (2013.01); A61B 5/0205 (2013.01); *H04M 2203/6027* (2013.01)

(58) Field of Classification Search
CPC ........ H04M 3/2281; H04M 2203/6027; A61B 5/0205
See application file for complete search history.

(56) References Cited

U.S. PATENT DOCUMENTS

| | | | |
|---|---|---|---|
| 9,492,084 B2 | 11/2016 | Behar et al. | |
| 9,781,247 B1 | 10/2017 | Gadepalli et al. | |
| 10,484,532 B1 * | 11/2019 | Newman | H04W 12/12 |
| 10,810,510 B2 * | 10/2020 | Baracaldo Angel | G06N 20/00 |
| 10,958,779 B1 * | 3/2021 | Rule | H04M 3/54 |
| 11,151,468 B1 * | 10/2021 | Chen | G06N 7/01 |
| 11,943,387 B1 * | 3/2024 | Wolinsky | H04M 3/2281 |
| 12,028,478 B2 * | 7/2024 | Trivedi | H04M 3/42221 |
| 2002/0170954 A1 | 11/2002 | Zingher et al. | |
| 2012/0127306 A1 | 5/2012 | Oh et al. | |
| 2012/0282878 A1 | 11/2012 | Amis | |
| 2016/0037292 A1 | 2/2016 | King | |
| 2016/0148488 A1 | 5/2016 | Tijerina et al. | |
| 2017/0142252 A1 * | 5/2017 | Bhupati | H04M 3/2281 |
| 2018/0225417 A1 * | 8/2018 | Bostick | G16H 30/40 |
| 2018/0336916 A1 * | 11/2018 | Baracaldo Angel | H04M 3/436 |
| 2019/0037081 A1 * | 1/2019 | Rao | H04M 7/0078 |
| 2019/0096216 A1 | 3/2019 | Eaton | |

(Continued)

FOREIGN PATENT DOCUMENTS

WO    WO-2020136367 A1 *    7/2020    ........ H04M 3/42025
WO    WO-2022106793 A1 *    5/2022

*Primary Examiner* — Adam D Houston
(74) *Attorney, Agent, or Firm* — Foley & Lardner LLP

(57) ABSTRACT

Disclosed aspects and embodiments pertain to customer distress assistance. A call can be detected to a callee from a caller. The call can be analyzed and determined to be a fraud or spam risk. In response, callee monitoring is triggered. The monitoring can capture biometrics or speech of the callee. Distress in the callee can be determined through analysis of the biometrics or speech and comparison to reference biometrics or speech of the callee. An individual associated with the callee can be selected based on determining the distress in the customer. The individual can be contacted through a notification or a call to assist the callee in distress.

20 Claims, 6 Drawing Sheets

(56) References Cited

U.S. PATENT DOCUMENTS

| | | | | |
|---|---|---|---|---|
| 2019/0373105 | A1* | 12/2019 | Kung | H04M 3/42059 |
| 2020/0202268 | A1* | 6/2020 | Retna | G06N 20/00 |
| 2020/0394887 | A1 | 12/2020 | Heath et al. | |
| 2021/0142640 | A1 | 5/2021 | Zhuang | |
| 2021/0383410 | A1* | 12/2021 | Talib | H04M 3/436 |
| 2022/0131973 | A1* | 4/2022 | Talib | H04M 3/2281 |
| 2022/0201030 | A1* | 6/2022 | Petit | H04L 63/20 |
| 2022/0367061 | A1* | 11/2022 | McInnis | G16H 40/63 |
| 2024/0031475 | A1* | 1/2024 | Shah | H04M 3/2281 |
| 2024/0146751 | A1* | 5/2024 | Tessler | H04L 63/1416 |
| 2024/0179241 | A1* | 5/2024 | Kucera | H04M 3/2281 |
| 2024/0232892 | A1* | 7/2024 | Kulasekaran | G06Q 20/4016 |
| 2024/0259492 | A1* | 8/2024 | Tessler | H04M 3/42059 |

* cited by examiner

CUSTOMER DISTRESS ASSISTANCE

BACKGROUND

Receiving a call from a fraudster or scammer can leave a receiver or callee feeling harassed or distressed. Frequently, the receiver is pressured to a point where the callee feels physically and psychologically distressed. In particular, the callee may reveal personal information such as financial accounts at a financial institution, social security numbers, personal identification numbers, or the like, leading them to feel considerable distress.

BRIEF SUMMARY OF THE DESCRIPTION

The following presents a simplified summary to provide a basic understanding of some aspects of the disclosed subject matter. This summary is not an extensive overview. It is not intended to identify necessary elements or delineate the scope of the claimed subject matter. Rather, this summary presents some concepts in a simplified form as a prelude to the more detailed description presented later.

According to one aspect, disclosed embodiments can include a system that comprises a processor coupled to a memory that includes instructions that, when executed by the processor, cause the processor to detect an incoming phone call, analyze a call conversation between a caller and a callee in real time with conversation analysis, classify the incoming phone call as a fraud risk based on the conversational analysis. Further, the instructions can cause the processor to trigger monitoring of a physical metric of the callee based on the classification of the fraud risk, compare the physical metric to a reference physical metric to determine a divergence between the physical metric and the reference physical metric, detect a sign of distress of the callee based on the divergence, select an individual associated with the callee after detection of the sign of distress, in which the individual is selected based on determining availability of a set of individuals, and send a notification in real time to the individual associated with the callee, wherein the notification reveals the sign of distress to the callee. The instructions can also cause the processor to collect biometric data from a sensor to monitor the physical metric. In addition, the instructions can cause the processor to invoke a conversational model trained to recognize problem words and phrases with natural language processing to classify the phone call as a fraud risk. The instructions can also cause the processor to detect the caller is originating from a blocklist source and classify the incoming phone call as a fraud risk. Further, the instructions can cause the processor to access the contact information of the individual and automatically join the individual in the phone call. The instructions can additionally cause the processor to activate a security control for the phone call that is a fraud risk. The security controls can include at least one of mute, interrupt prompt, forced disconnect, or automated transfer of the phone call to the individual. Furthermore, the instructions can cause the processor to access social media data of the individual to determine availability and collect biometric data from a wearable device to monitor the physical metric.

In accordance with another aspect, disclosed embodiments can include a method comprising executing, on a processor, instructions that cause the processor to perform operations. The operations include detecting an incoming call, analyzing a conversation between a caller and a callee in real time with conversation analysis, classifying the incoming call as a fraud risk to a callee based on the conversation analysis, triggering monitoring of a physical metric of the callee in response to classification of the incoming call as a fraud risk, and comparing the physical metric to a reference physical metric to determine a divergence between the physical metric and the reference physical metric. The operations can further comprise detecting a sign of distress of the callee based on the divergence, selecting an individual associated with the callee after detection of the sign of distress, in which the individual is selected from a set of available individuals associated with the callee, and transmitting a notification in real time to a selected individual that reveals the sign of distress of the callee. In one instance, the monitoring can comprise collecting biometric data from the callee from a sensor, such as a sensor of a wearable device. Analyzing the conversation can also comprise invoking a conversational model trained to recognize problem words and phrases with natural language processing to classify the call as a fraud risk. The operations can further comprise detecting the incoming call originates from a source that is on a blocklist of known fraudulent callers and classifying the incoming call as fraudulent. Further, operation can comprise determining availability of an individual based on social media data of the individual. The operations can also include accessing contact information of the individual that is selected and joining the individual to the call with the caller and callee. Furthermore, the operations can comprise activating a security control for the callee that blocks transactions to a financial account of the callee.

According to yet another aspect, disclosed embodiments can include a method of distress assistance. The method can comprise detecting an incoming call with a call manager executing on a computing device, analyzing a conversation between a caller and callee in near real time, and classifying the incoming call as a spam risk based on conversation analysis. The method can next comprise automatically triggering, by the call manager, monitoring of a physical metric of the callee based on the classification of the spam risk, detecting distress of the callee based on divergence of the physical metric of the callee from a reference physical metric, selecting an individual associated with the callee in response to detecting the distress, in which the individual is selected based on determining availability of a set of individuals, and sending a notification of the distress of the callee in near-real time to a selected individual. The act of analyzing the conversation can further comprise monitoring a voice characteristic of the callee, comparing the voice characteristic of the callee to a voice profile characteristic of the callee, detecting a distress sentiment based on determining a difference between the voice characteristic and the voice profile characteristic, and identifying distress of the callee based on the distress sentiment. Further, the method can comprise pausing the conversation between the caller and the callee and calling the individual selected to provide assistance to the callee. The method can also comprise activating a security control to at least one of mute, interrupt prompt, or forced disconnect of the call in response to classification as a spam risk.

In aspects, the subject disclosure provides substantial benefits in terms of distress assistance. One advantage resides in detecting distress during a spam risk call. Another advantage resides in an automatic process to assist in mitigating or eliminating distress.

To accomplish the foregoing and related ends, certain illustrative aspects of the claimed subject matter are described herein in connection with the following description and the annexed drawings. These aspects indicate various ways in which the subject matter may be practiced, all of which are intended to be within the scope of the disclosed subject matter. Other advantages and novel features may become apparent from the following detailed description when considered in conjunction with the drawings.

BRIEF DESCRIPTION OF THE DRAWINGS

Aspects of the disclosure are understood from the following detailed description when read with the accompanying drawings. It will be appreciated that elements, structures, or the like of the drawings are not necessarily drawn to scale. Accordingly, the dimensions of the same may be arbitrarily increased or reduced for clarity of discussion, for example.

DETAILED DESCRIPTION

Various aspects of the subject disclosure are now described in more detail with reference to the annexed drawings, wherein like numerals generally refer to like or corresponding elements throughout. In the following description, for purposes of explanation, numerous specific details are set forth in order to provide a thorough understanding of the aspects of this disclosure. It may be evident, however, that the aspects can be practiced without these specific details. In other instances, well-known structures and devices are shown in block diagram form in order to facilitate clarity and understanding.

As used in this application, the terms "component", "module," "system", "interface", and the like are generally intended to refer to a computer-related entity, either hardware, a combination of hardware and software, software, or software in execution. For example, a component may be, but is not limited to being, a process running on a processor, a processor, an object, an executable, a thread of execution, a program, or a computer. By way of illustration, both an application running on a controller and the controller can be a component. One or more components can reside within a process or thread of execution, and a component may be localized on one computer or distributed between two or more computers.

Furthermore, the claimed subject matter can be implemented as a method, apparatus, or article of manufacture using standard programming or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, many modifications may be made to this configuration without departing from the scope or spirit of the claimed subject matter.

Figure 1:
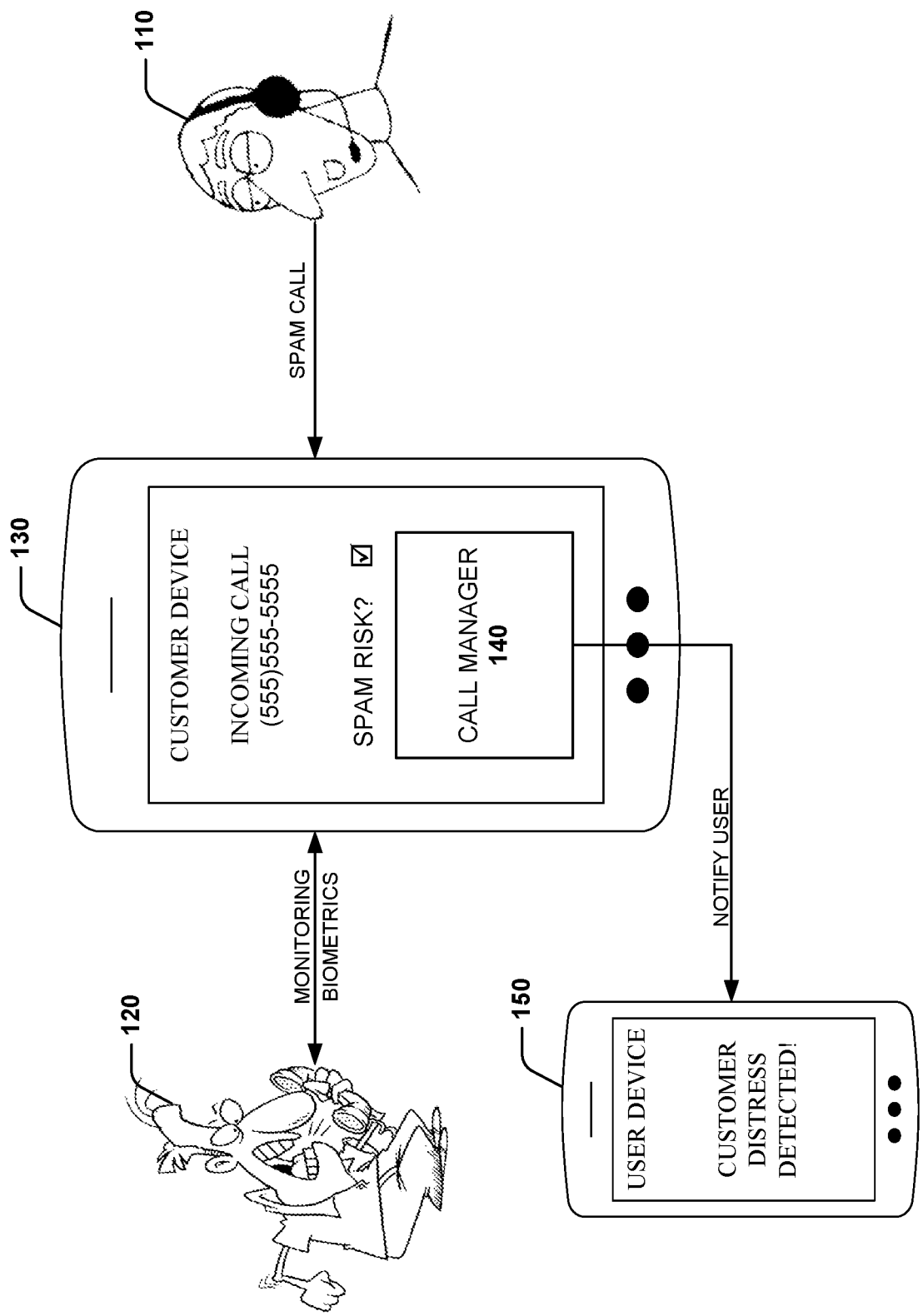
FIG. 1 illustrates a high-level diagram of an example implementation.

Referring initially to FIG. 1, a high-level overview of an example implementation is depicted. A fraud or spam caller 110 can place a call to a customer or callee 120 through a customer device 130. The customer device 130 can be a mobile phone, personal computer, wearable device, Internet of Things device, and/or the like. The customer device 130 can include a call manager 140. The call manager 140 can monitor calls to the customer device 130. The call manager 140 monitors calls to detect a spam risk call to the customer 120 on the customer device 130. The call manager 140 can determine a spam risk call in real time or near real time. For example, the spam caller 110 can call the customer 120, and the call manager 140 can determine the call is a spam risk call while the call is being conducted between the spam caller 110 and the customer 120.

In some embodiments, the call manager 140 trains a conversation model. The conversation model can analyze conversations in real time or near real time for problem words or phrases. The conversation model can classify the call as a spam risk call upon detecting a problem word or phrase. For example, the call manager 140 can detect the phrase "I need your bank account number." The call manager 140, via the conversation model, can classify the call as a spam risk call based on the detected phrase. In some embodiments, the call manager 140 can utilize a natural language processing technique, a neural network, artificial intelligence, machine learning, and/or the like to detect the problem words or phrases via the conversation model.

In some embodiments, the call manager 140 can detect a spam call risk via determining the call source. The call manager 140 can determine the call source and compare the call source to a list of blocklist sources of known spam callers or spam call originators. The call manager 140 can classify the call as a spam risk call upon determining a match of the call source and a listing of the blocklist sources.

The call manager 140 can trigger monitoring of the customer 120 based on detection or classification of the spam risk call. The call manager 140 can monitor physiological metrics, biometrics, physical metrics, and/or psychological metrics of the customer 120, such as pulse, sweating, speech, loudness, other biometrics, and/or the like. In some embodiments, the call manager 140 can utilize readings of the customer 120 via from the customer device 130. For example, the call manager 140 can monitor rate of speech captured by the customer device 130 during the call to determine psychological distress of the customer 120. In other embodiments, the call manager 140 can interface with a wearable device, an internet of things device, and/or the like to retrieve physical and/or psychological metrics of the customer 120. For example, the call manager 140 can interface with a smart ring worn on a finger of the customer 120 to retrieve pulse data. The call manager 140 can determine an elevated pulse rate to determine whether the customer is in distress due to the spam risk call.

The call manager 140 can analyze captured or retrieved biometrics to determine the customer 120 is distressed. The call manager 140 can compare the biometrics to a reference biometric to determine an abnormality indicative of distress. For example, the call manager 140 can detect a heart rate of 120 beats per minute in comparison to a normal resting heart rate of the customer 120 of 60 beats per minute. The call manager 140 can determine that the customer 120 is in distress based on the comparison and a divergence of the heart rate from the normal resting heart rate. In some embodiments, the call manager 140 can determine a delta or change in biometrics to determine stress. For example, the call manager 140 can determine that the heart rate of the customer 120 is increasing by ten beats per minute since the commencement of the call. The call manager 140 can compare the change to a threshold change to determine distress in the customer 120.

The call manager 140 can contact or organize contact with a user. The user can be a friend of the customer 120, an associate of the customer 120, a medical professional, an emergency response person, law enforcement, and/or the like. The call manager 140 can arrange contact with the user based on the detection of distress of the customer 120. In some embodiments, the call manager 140 determines the user from a plurality of users to contact. The call manager 140 can determine or train a selection model for determining which user to contact upon detecting distress of the customer 120. The selection model can be trained to select the user according to different constraints. For example, the selection model can select the user based on availability, time of day, day of week, distance, schedule, calendar entry, and/or the like. For example, the selection model can access a calendar of a potential user and determine that the potential user has a present appointment that could conflict with them helping the customer 120. The selection model can determine a different user to contact based on the calendar entry. In some embodiments, the selection model can follow predetermined business rules to select the user to contact. For example, a business rule can be to select the closest present distanced friend of the customer 120 to contact. In another example, a business rule can be to contact the local emergency medical service for a wellness check.

The call manager 140 can contact the user via a user device 150. The user device 150 can be a mobile phone, personal computer, wearable device, Internet of Things device, and/or the like associated with the user. The call manager 140 can determine or access contact information of the user. The call manager 140 can generate and send a notification to the user device 150, implement a call to the user device 150, and/or the like. For example, the call manager 140 can send an SMS text message to the user device 150. The notification can include instructions for the user to contact the customer 120. In some embodiments, the call manager 140 can pause or hold the spam risk call and place a call to the user device 150.

Figure 2:
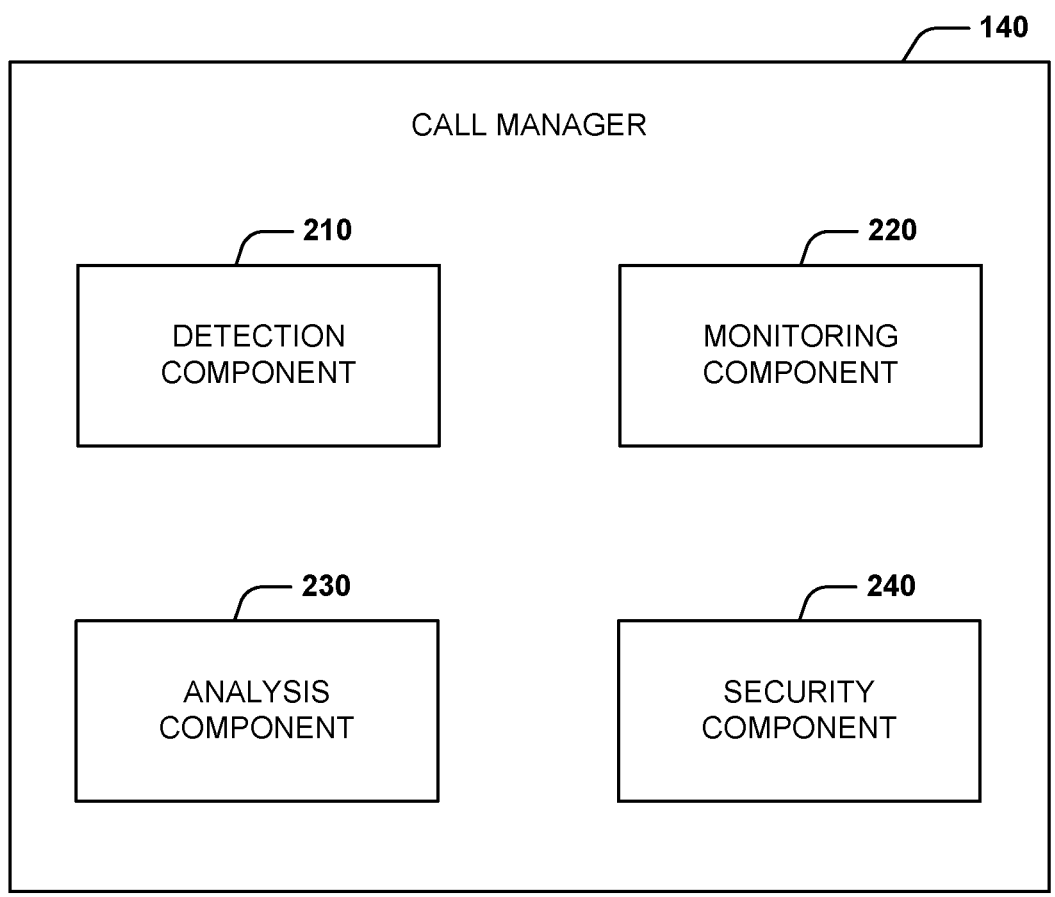
FIG. 2 illustrates an example component diagram of a call manager.

FIG. 2 illustrates a detailed component diagram of the call manager 140. The call manager 140 can include a detection component 210. The detection component 210 can monitor calls to the customer device 130. The detection component 210 monitors calls to detect a spam risk call to the customer 120 on the customer device 130. The detection component 210 can determine a spam risk call in real time or near real time. For example, the spam caller 110 can call the customer 120, and the detection component 210 can determine the call is a spam risk call while the call is being conducted between the spam caller 110 and the customer 120.

In some embodiments, the detection component 210 can detect a spam call risk via determining the call source. The detection component 210 can determine the call source and compare the call source to a list of blocklist of sources that are known to be spam call originators. The detection component 210 can classify the call as a spam risk call upon determining a match of the call source and a listing on the blocklist of sources.

In some embodiments, the detection component 210 trains a conversation model. The conversation model can analyze conversations in real time or near real time for problem words or phrases. The conversation model can classify the call as a spam risk call upon detecting a problem word or phrase. For example, the detection component 210 can detect the phrase "I need your password." The detection component 210 via the conversation model can classify the call as a spam risk call based on the detected phrase. In some embodiments, the detection component 210 can utilize natural language processing, a neural network, artificial intelligence, machine learning, and/or the like to detect the problem words or phrases via the conversation model.

The detection component 210 determines a conversation model based on an analysis of previous spam risk calls. The detection component 210 can train the conversation model via words and/or phrases within a spam risk call. The detection component 210 can utilize a machine learning technique to determine trends between words and/or phrases and classifications of calls as spam risks. The model component learns from existing data to make predictions about spam risk calls to the customer 120. The detection component 210 builds the conversation model from the previous spam risk calls (e.g., "training data set") in order to make data-driven predictions or decisions expressed as outputs or assessments for the customer 120. The detection component 210 can determine the trends and/or correlations within previous spam risk calls. In some embodiments, the detection component 210 utilizes the machine learning technique to analyze the previous spam risk calls across different customers to determine a conversation model based on correlations in the previous spam risk calls.

In some embodiments, the detection component 210 trains the conversation model with previous spam risk calls and captured biometrics of the customer 120 and/or other customers. The conversation model can determine correlations between words and/or phrases and abnormal biometrics of the customer 120 to determine spam risk calls and/or distress of the customer 120. For example, the phrase "What is your social security number?" can be correlated with observed elevated heart rates. The conversation model can be trained to predict distress of the customer 120 on capturing the phrase in a present spam risk call.

The call manager 140 includes a monitoring component 220. The monitoring component 220 can trigger monitoring of the customer 120 based on detection or classification of the spam risk call. The monitoring component 220 can monitor physical metrics and/or psychological metrics of the customer 120, such as pulse, sweating, speech, loudness, other biometrics, and/or the like. In some embodiments, the monitoring component 220 can utilize readings of the customer 120 via the customer device 130. For example, the monitoring component 220 can monitor rate of speech captured by the customer device 130 during the call to determine psychological distress of the customer 120. In other embodiments, the monitoring component 220 can interface with a wearable device, an internet of things device, and/or the like to retrieve physical and/or psychological metrics of the customer 120. For example, the call manager 140 can interface with a smart watch worn on a wrist of the customer 120 to retrieve pulse data. The monitoring component 220 can determine an elevated pulse rate to determine the customer 120 is in distress due to the spam risk call.

The call manager 140 includes an analysis component 230. The analysis component 230 can analyze captured or retrieved biometrics to determine the customer 120 is distressed. The analysis component 230 can compare the biometrics to a reference biometric to determine an abnormality indicative of distress. For example, the analysis component 230 can detect a heart rate of 125 beats per minute in comparison to a normal resting heart rate of the customer 120 of 60 beats per minute. The analysis component 230 can determine that the customer 120 is in distress based on the comparison and divergence of the heart rate from the normal resting heart rate. In some embodiments, the analysis component 230 can determine a delta or change in biometrics to determine stress. For example, the analysis component 230 can determine that the heart rate of the customer 120 is increasing by ten beats per minute since the commencement of the call. The analysis component 230 can compare the change to a threshold change to determine distress in the customer 120.

The call manager 140 includes a security component 240. The security component 240 can contact or organize contact with the user. The security component 240 can arrange contact with the user based on the detection of distress of the customer 120. In some embodiments, the security component 240 determines the user from a plurality of users to contact. In some embodiments, the security component 240 can determine or train a selection model for determining which user to contact upon detecting distress of the customer 120. The selection model can be trained to select the user according to different constraints. For example, the selection model can select the user based on availability, time of day, day of week, distance, schedule, calendar entry, social media status, and/or the like. For example, the selection model can access a social media feed of a potential user and determine that the potential user has a present status that could conflict with them helping the customer 120. The selection model can determine a different user to contact based on the social media status that indicates the user is available or unavailable. For example, the security component 240 can access a social media feed of the customer 120 and/or the user. The security component 240 can determine location, availability, and/or the like based on social media data of users associated with the customer 120. For example, a user can post "Watching a movie at the movie theater." The security component 240 can determine that the user is not available or too far away from the customer 120 to provide assistance to the customer 120.

In some embodiments, the selection model can follow predetermined business rules to select the user to contact. For example, a business rule can be to select the closest related relative of the customer 120 to contact. In another example, a business rule can be to contact a psychologist associated with the customer 120. In other embodiments, the selection model can follow a prioritized list of users to assist the customer 120.

The security component 240 can contact the user via a user device 150. The security component 240 can generate and send a notification to the user device 150, implement a call to the user device 150, and/or the like. For example, the security component 240 can send a push notification to the user device 150. The notification can include instructions for the user to contact the customer 120. In some embodiments, the security component 240 can pause or hold the spam risk call and place a call to the user device 150. In some embodiments, the security component 240 can implement further security controls onto the spam risk call. The security controls can automatically mute the customer 120 and/or the spam caller 110, an audio or video interrupt prompt via the customer device 130, a forced disconnect of the spam risk call, an automated transfer of the spam risk call to the user, automatically teleconferencing the user to join the user to the spam risk call, and/or the like. For example, the security component 240 can connect the user via the user device 150 to the customer device 130 such that the user joins the spam risk call and provide assistance to the customer 120.

Figure 3:
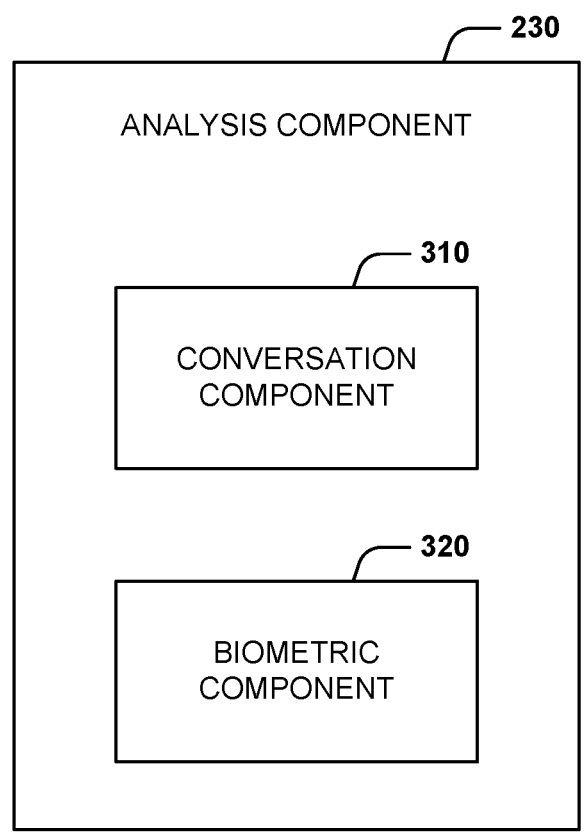
FIG. 3 illustrates an example component diagram of an analysis component.

FIG. 3 illustrates a detailed component diagram of an analysis component 230. The analysis component 230 includes a conversation component 310 that can perform a conversation analysis. The conversation component 310 can analyze an ongoing conversation or ongoing/incoming call between the customer 120 and the spam caller 110 on the spam risk call. The conversation component 310 can analyze the voice of the customer 120 for signs of distress. The conversation component 310 can analyze the voice for behavioral patterns, speech patterns, a voice profile, a rate of speech, and/or the like. The conversation component 310 can compare the voice to a reference voice or voice metrics to determine abnormal signs or a difference between them that can be attributed to distress of the customer 120. The conversation component 310 can compare the voice to a known voice profile of the customer 120 that was captured in non-distressed time. In other embodiments, the conversation component 310 can analyze the conversation to determine sentiment. The conversation component 310 can determine a distress sentiment based on the sentiment analysis for the customer 120. The conversation component 310 can further determine and/or confirm the spam risk call by determining a negative sentiment or dishonest sentiment of the spam caller 110.

The analysis component 230 can include a biometric component 320. The biometric component 320 can analyze captured or retrieved biometrics to determine the customer 120 is distressed. The biometric component 320 can compare the biometrics to a reference biometric to determine an abnormality indicative of distress (e.g., divergence or a difference between the biometrics and the reference biometric). For example, the biometric component 320 can detect a skin moisture level in comparison to a normal moisture level of the customer 120. The biometric component 320 can determine that the customer 120 is in distress based on the comparison and a divergence of the skin moisture level indicative of perspiration from the normal moisture level. In some embodiments, the biometric component 320 can determine a delta or change in biometrics to determine stress. For example, the biometric component 320 can determine that the skin moisture level of the customer 120 is increasing since the commencement of the call. The biometric component 320 can compare the change to a threshold change to determine distress in the customer 120.

Figure 4:
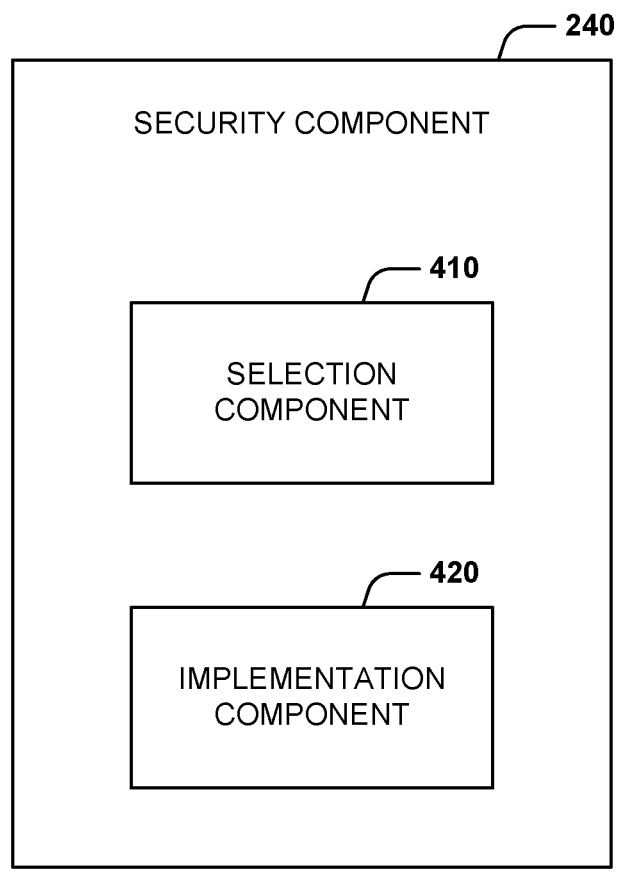
FIG. 4 illustrates an example component diagram of a security component.

FIG. 4 illustrates an example component diagram of a security component 240. The security component 240 includes a selection component 410. The selection component 240 can contact or organize contact with a user. The selection component 240 can arrange contact with the user based on the detection of distress of the customer 120. In some embodiments, the selection component 240 determines the user from a plurality of users to contact.

In some embodiments, the selection component 240 can determine or train a selection model for determining which user to contact upon detecting distress of the customer 120. The selection model can be trained to select the user according to different constraints. For example, the selection component 410 can select the user based on availability, time of day, day of week, distance, schedule, calendar entry, social media status, demographic of the customer 120, other customer information, and/or the like. For example, the selection model can determine a competency level of the customer 120. The competency level of the customer 120 can be based on demographic information of the customer 120 and/or other customer information. For example, the selection model can determine a lower competency level for a customer 120 that has an age higher than 90 years old. The selection component 410 via the selection model can factor in the competency level of the customer 120 to select the user based on the competency level. For example, the selection component 410 may select a law enforcement officer as the user to contact for the customer 120 with a lower competency level. The selection component 410 can determine a different user to contact based on a higher determined competency level of the customer 120. For example, the selection component 410 can select a neighbor as the user to assist the customer 120 instead of a law enforcement officer.

The security component 240 includes an implementation component 420. The implementation component 420 can contact the user via a user device 150. The implementation component 420 can generate and send a notification to the user device 150, implement a call to the user device 150, and/or the like. For example, the implementation component 420 can send a push notification to the user device 150. The notification can include instructions for the user to contact the customer 120. The notification reveals the sign(s) of distress of the customer 120. In some embodiments, the implementation component 420 can pause or hold the spam risk call and place a call to the user device 150. In some embodiments, the implementation component 420 can implement further security controls onto the spam risk call. The security controls can automatically mute the customer 120 and/or the spam caller 110, an audio or video interrupt prompt via the customer device 130, a forced disconnect of the spam risk call, an automated transfer of the spam risk call to the user, automatically teleconferencing the user to join the user to the spam risk call, and/or the like. For example, the implementation component 420 can connect the user via the user device 150 to the customer device 130 such that the user joins the spam risk call and provide assistance to the customer 120.

In some embodiments, the implementation component 420 can perform further security controls. The implementation component 420 can contact a financial institution, block transactions to a financial account, lock a financial account of the customer 120, trigger identity monitoring, freeze credit score, determine a credit report, and/or the like. For example, the implementation component 420 can interface with a financial institution to prevent transactions for a period during and/or after the spam risk call.

Figure 5:
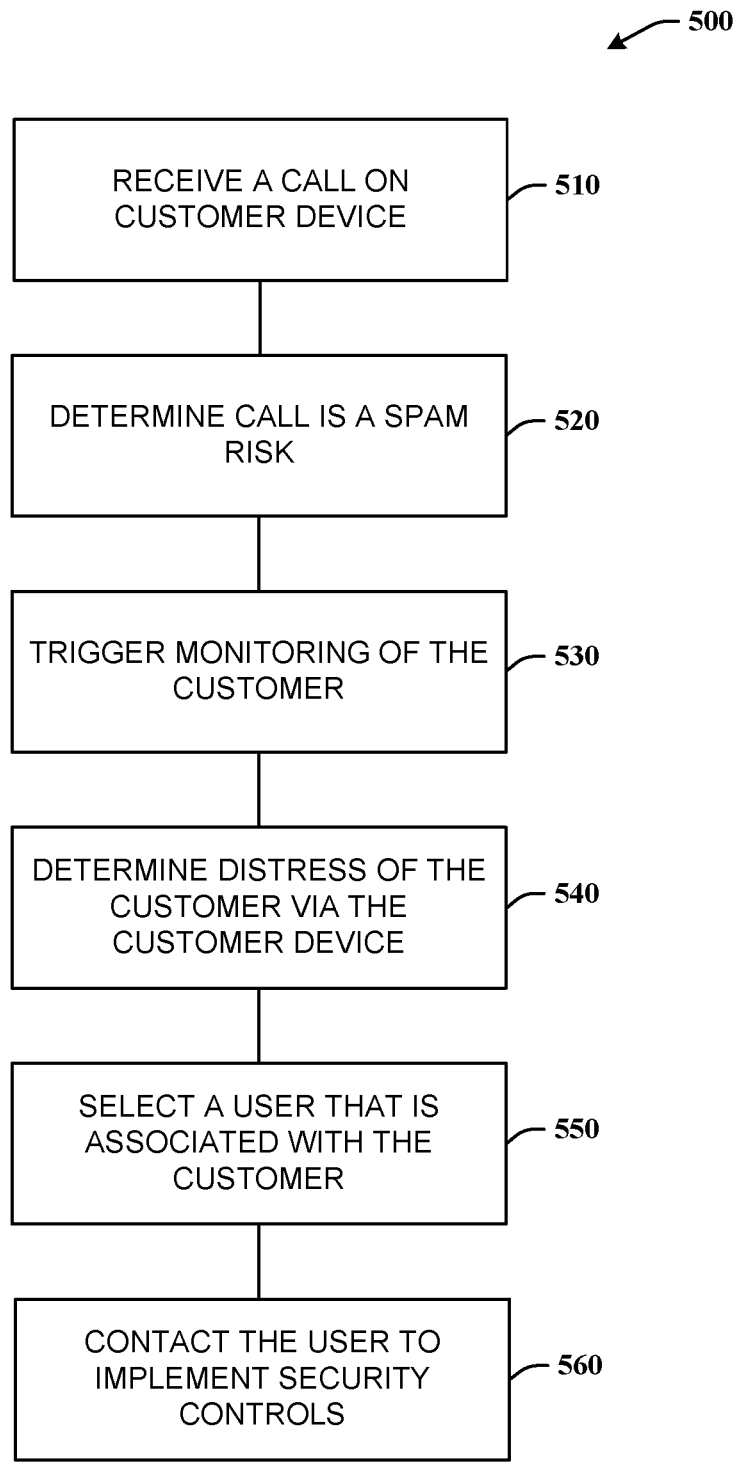
FIG. 5 illustrates a method for customer distress assistance.

In view of the example systems described above, methods that can be implemented in accordance with the disclosed subject matter will be better appreciated with reference to the flow chart diagram of FIG. 5. While, for purposes of simplicity of explanation, the methods show and describe a series of blocks, it is to be understood and appreciated that the disclosed subject matter is not limited by the order of the blocks, as some blocks can occur in different orders or concurrently with other blocks from what is depicted and described herein. Moreover, not all illustrated blocks may be required to implement the methods described hereinafter. Further, each block or combination of blocks can be implemented by computer program instructions that can be provided to a processor to produce a machine, such that the instructions executing on the processor create a means for implementing functions specified by a flow chart block. It is also appreciated that the method 500 is described in conjunction with a specific example for explanation purposes.

FIG. 5 illustrates a method 500 for customer distress assistance. At 510, a call can be received to a customer device 120 from a spam caller 110. For example, the scammer can place a call to the customer 120 on their customer device 120. At 520, the call can be determined to be a spam risk call. The call manager 140 can analyze the conversation during the call to determine if it is a spam risk call. At 530, monitoring of the customer 120 can be triggered. The call manager 140 can begin monitoring biometrics and/or speech of the customer 120 based on the determination of the spam risk call.

At 540, distress of the customer 120 can be determined. The call manager 140 can analyze the biometrics of the customer 120 to determine abnormal characteristics that are indicative of distress. At 550, a user associated with the customer can be selected. The call manager 140 can determine a most appropriate user associated with the customer, such as a friend, neighbor, medical professional, law enforcement officer, and/or the like. At 560, the user is contacted to assist the customer 120. The call manager 140 can send a notification or place a call to the user to assist the customer 120 that is in distress.

The terms "caller" and "callee" have been utilized herein to respectively refer to a person who initiates a phone call and a person who receives the phone call. Further, a callee has been referred to as a customer, wherein the person is a customer of a distress mitigation system or service or a customer of an entity that provides such functionality (e.g., a financial institution). One scenario involves a caller being a fraudster or spammer who targets a callee for fraud or unsolicited commercial messages. In other words, the caller can cause the callee distress by seeking to defraud the callee in some manner including unsolicited sales calls. However, the caller need not cause distress. In fact, the distress can be due to circumstances that are independent of fraudsters or spammers. For example, the distress can be a result of a death in the family or financial trouble. In this scenario, the caller is the person that is distressed and seeking to work with a financial institution or other person or entity to address a situation. Aspects of the disclosure pertaining to mitigating distress can also be employed in this situation as well.

As used herein, the terms "component" and "system," as well as various forms thereof (e.g., components, systems, sub-systems) are intended to refer to a computer-related entity, either hardware, a combination of hardware and software, software, or software in execution. For example, a component may be, but is not limited to being, a process running on a processor, a processor, an object, an instance, an executable, a thread of execution, a program, and/or a computer. By way of illustration, both an application running on a computer and the computer can be a component. One or more components may reside within a process and/or thread of execution, and a component may be localized on one computer and/or distributed between two or more computers.

The conjunction "or" as used in this description and appended claims is intended to mean an inclusive "or" rather than an exclusive "or," unless otherwise specified or clear from context. In other words, "'X' or 'Y'" is intended to mean any inclusive permutations of "X" and "Y." For example, if "'A' employs 'X,'" "'A employs 'Y,'" or "'A' employs both 'X' and 'Y,'" then "'A' employs 'X' or 'Y'" is satisfied under any of the foregoing instances.

Furthermore, to the extent that the terms "includes," "contains," "has," "having" or variations in form thereof are used in either the detailed description or the claims, such terms are intended to be inclusive in a manner similar to the term "comprising" as "comprising" is interpreted when employed as a transitional word in a claim.

Figure 6:
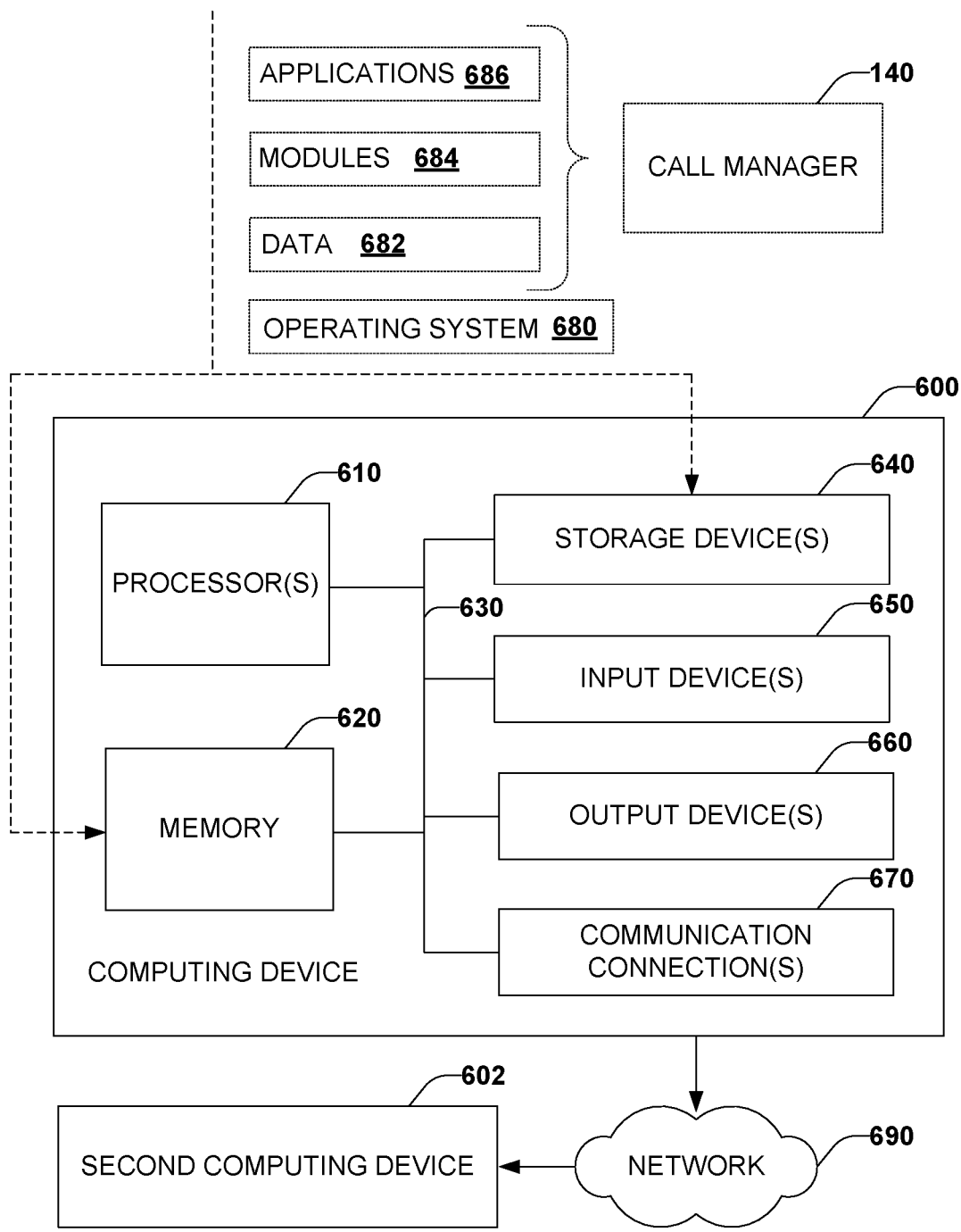
FIG. 6 illustrates a computing environment where one or more of the provisions set forth herein can be implemented, according to some embodiments.

To provide a context for the disclosed subject matter, FIG. 6, as well as the following discussion, are intended to provide a brief, general description of a suitable environment in which various aspects of the disclosed subject matter can be implemented. The suitable environment, however, is solely an example and is not intended to suggest any limitation on the scope of use or functionality.

While the above-disclosed system and methods can be described in the general context of computer-executable instructions of a program that runs on one or more computers, those skilled in the art will recognize that aspects can also be implemented in combination with other program modules or the like. Generally, program modules include routines, programs, components, data structures, among other things, that perform particular tasks and/or implement particular abstract data types. Moreover, those skilled in the art will appreciate that the above systems and methods can be practiced with various computer system configurations, including single-processor, multi-processor or multi-core processor computer systems, mini-computing devices, server computers, as well as personal computers, hand-held computing devices (e.g., personal digital assistant (PDA), smartphone, tablet, watch . . . ), microprocessor-based or programmable consumer or industrial electronics, and the like. Aspects can also be practiced in distributed computing environments where tasks are performed by remote processing devices that are linked through a communications network. However, some, if not all aspects, of the disclosed subject matter can be practiced on stand-alone computers. In a distributed computing environment, program modules may be located in one or both of local and remote memory devices.

With reference to FIG. 6, illustrated is an example computing device 600 (e.g., desktop, laptop, tablet, watch, server, hand-held, programmable consumer or industrial electronics, set-top box, game system, compute node . . . ). The computing device 600 includes one or more processor(s) 610, memory 620, system bus 630, storage device(s) 640, input device(s) 650, output device(s) 660, and communications connection(s) 670. The system bus 630 communicatively couples at least the above system constituents. However, the computing device 600, in its simplest form, can include one or more processors 610 coupled to memory 620, wherein the one or more processors 610 execute various computer executable actions, instructions, and or components stored in the memory 620.

The processor(s) 610 can be implemented with a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any processor, controller, microcontroller, or state machine. The processor(s) 610 may also be implemented as a combination of computing devices, for example, a combination of a DSP and a microprocessor, a plurality of microprocessors, multi-core processors, one or more microprocessors in conjunction with a DSP core, or any other such configuration. In one embodiment, the processor(s) 610 can be a graphics processor unit (GPU) that performs calculations with respect to digital image processing and computer graphics.

The computing device 600 can include or otherwise interact with a variety of computer-readable media to facilitate control of the computing device to implement one or more aspects of the disclosed subject matter. The computer-readable media can be any available media accessible to the computing device 600 and includes volatile and nonvolatile media, and removable and non-removable media. Computer-readable media can comprise two distinct and mutually exclusive types, namely storage media and communication media.

Storage media includes volatile and nonvolatile, removable, and non-removable media implemented in any method or technology for storage of information such as computer-readable instructions, data structures, program modules, or other data. Storage media includes storage devices such as memory devices (e.g., random access memory (RAM), read-only memory (ROM), electrically erasable programmable read-only memory (EEPROM) . . . ), magnetic storage devices (e.g., hard disk, floppy disk, cassettes, tape . . . ), optical disks (e.g., compact disk (CD), digital versatile disk (DVD) . . . ), and solid state devices (e.g., solid state drive (SSD), flash memory drive (e.g., card, stick, key drive . . . ) . . . ), or any other like mediums that store, as opposed to transmit or communicate, the desired information accessible by the computing device 600. Accordingly, storage media excludes modulated data signals as well as that described with respect to communication media.

Communication media embodies computer-readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency (RF), infrared, and other wireless media.

The memory 620 and storage device(s) 640 are examples of computer-readable storage media. Depending on the configuration and type of computing device, the memory 620 may be volatile (e.g., random access memory (RAM)), nonvolatile (e.g., read only memory (ROM), flash memory . . . ) or some combination of the two. By way of example, the basic input/output system (BIOS), including basic routines to transfer information between elements within the computing device 600, such as during start-up, can be stored in nonvolatile memory, while volatile memory can act as external cache memory to facilitate processing by the processor(s) 610, among other things.

The storage device(s) 640 include removable/non-removable, volatile/nonvolatile storage media for storage of vast amounts of data relative to the memory 620. For example, storage device(s) 640 include, but are not limited to, one or more devices such as a magnetic or optical disk drive, floppy disk drive, flash memory, solid-state drive, or memory stick.

Memory 620 and storage device(s) 640 can include, or have stored therein, operating system 680, one or more applications 686, one or more program modules 684, and data 682. The operating system 680 acts to control and allocate resources of the computing device 600. Applications 686 include one or both of system and application software and can exploit management of resources by the operating system 680 through program modules 684 and data 682 stored in the memory 620 and/or storage device(s) 640 to perform one or more actions. Accordingly, applications 686 can turn a general-purpose computer 600 into a specialized machine in accordance with the logic provided thereby.

All or portions of the disclosed subject matter can be implemented using standard programming and/or engineering techniques to produce software, firmware, hardware, or any combination thereof to control the computing device 600 to realize the disclosed functionality. By way of example and not limitation, all or portions of the call manager 140 can be, or form part of, the application 686, and include one or more modules 684 and data 682 stored in memory and/or storage device(s) 640 whose functionality can be realized when executed by one or more processor(s) 610.

In accordance with one particular embodiment, the processor(s) 610 can correspond to a system on a chip (SOC) or like architecture including, or in other words integrating, both hardware and software on a single integrated circuit substrate. Here, the processor(s) 610 can include one or more processors as well as memory at least similar to the processor(s) 610 and memory 620, among other things. Conventional processors include a minimal amount of hardware and software and rely extensively on external hardware and software. By contrast, an SOC implementation of a processor is more powerful, as it embeds hardware and software therein that enable particular functionality with minimal or no reliance on external hardware and software. For example, the call manager 140 and/or functionality associated therewith can be embedded within hardware in a SOC architecture.

The input device(s) 650 and output device(s) 660 can be communicatively coupled to the computing device 600. By way of example, the input device(s) 650 can include a pointing device (e.g., mouse, trackball, stylus, pen, touchpad), keyboard, joystick, microphone, voice user interface system, camera, motion sensor, and a global positioning satellite (GPS) receiver and transmitter, among other things. The output device(s) 660, by way of example, can correspond to a display device (e.g., liquid crystal display (LCD), light emitting diode (LED), plasma, organic light-emitting diode display (OLED)), speakers, voice user interface system, printer, and vibration motor, among other things. The input device(s) 650 and output device(s) 660 can be connected to the computing device 600 by way of wired connection (e.g., bus), wireless connection (e.g., Wi-Fi, Bluetooth), or a combination thereof.

The computing device 600 can also include communication connection(s) 670 to enable communication with at least a second computing device 602 by means of a network 690. The communication connection(s) 670 can include wired or wireless communication mechanisms to support network communication. The network 690 can correspond to a local area network (LAN) or a wide area network (WAN) such as the Internet. The second computing device 602 can be another processor-based device with which the computing device 600 can interact. For example, the computing device 600 can correspond to a server that executes functionality of the call manager 140, and the second computing device 602 can be a user device that communicates and interacts with the computing device 600.

What has been described above includes examples of aspects of the claimed subject matter. It is, of course, not possible to describe every conceivable combination of components or methodologies for purposes of describing the claimed subject matter, but one of ordinary skill in the art may recognize that many further combinations and permutations of the disclosed subject matter are possible. Accordingly, the disclosed subject matter is intended to embrace all such alterations, modifications, and variations that fall within the spirit and scope of the appended claims.

What is claimed is:

1. A system, comprising:
a processor coupled to a memory that includes instructions that, when executed by the processor, cause the processor to:
detect an incoming phone call;
analyze the incoming phone call between a caller and a callee in real time with conversational analysis;
classify the incoming phone call as a fraud risk based on the conversational analysis;
trigger monitoring of a physical metric of the callee based on the classification of the incoming call as a fraud risk;
compare the physical metric to a reference physical metric to determine a divergence between the physical metric and the reference physical metric;
detect a sign of distress of the callee based on the divergence;
select an individual associated with the callee after detection of the sign of distress, wherein the individual is selected based on determining availability of a set of individuals; and
send a notification in real time to the individual associated with the callee, wherein the notification reveals the sign of distress to the callee.

2. The system of claim 1, wherein the instructions further cause the processor to collect biometric data from a sensor to monitor the physical metric.

3. The system of claim 1, wherein the instructions further cause the processor to invoke a conversational model trained to recognize problem words and phrases with natural language processing to classify the phone call as a fraud risk.

4. The system of claim 1, wherein the instructions further cause the processor to:
detect the caller is originating from a blocklist source; and
classify the incoming phone call as a fraud risk based on the conversational analysis and the detection of the caller as originating from the blocklist source.

5. The system of claim 1, wherein the instructions further cause the processor to:
access contact information of the individual; and
automatically join the individual to the phone call.

6. The system of claim 1, wherein the instructions further cause the processor to activate a security control for the phone call that is a fraud risk, wherein the security control is one of mute, interrupt prompt, forced disconnect, or automated transfer of the phone call to the individual.

7. The system of claim 1, wherein the instructions further cause the processor to access social media data of the individual to determine availability.

8. The system of claim 1, wherein the instructions further cause the processor to collect biometric data from a wearable device to monitor the physical metric.

9. A method, comprising:
executing, on a processor, instructions that cause the processor to perform operations, the operations comprising:
detecting an incoming call;
analyzing a conversation between a caller and a callee in real time with conversation analysis;
classifying the incoming call as a fraud risk to a callee based on the conversation analysis;
triggering monitoring of a physical metric of the callee in response to the classification of the incoming call as a fraud risk;
comparing the physical metric to a reference physical metric to determine a divergence between the physical metric and the reference physical metric;

detecting a sign of distress of the callee based on the divergence;

selecting an individual associated with the callee after detection of the sign of distress, wherein the individual is selected from a set of available individuals associated with the callee; and transmitting a notification in real time to a selected individual that reveals the sign of distress of the callee.

10. The method of claim 9, wherein the monitoring comprises collecting biometric data from the callee from a sensor.

11. The method of claim 10, further comprising collecting the biometric data from a sensor of a wearable device.

12. The method of claim 9, wherein analyzing the conversation comprises invoking a conversational model trained to recognize problem words and phrases with natural language processing to classify the call as a fraud risk.

13. The method of claim 9, wherein the operations further comprise:

detecting the incoming call originates from a source that is on a blocklist of known fraudulent callers; and classifying the incoming call as fraudulent based on the conversation analysis and the detection of the incoming call as originating from the source.

14. The method of claim 9, wherein the operations further comprise determining availability of an individual based on social media data of the individual.

15. The method of claim 9, wherein the operations further comprise:

accessing contact information of the individual that is selected; and joining the individual to the call with the caller and callee.

16. The method of claim 9, wherein the operations further comprise activating a security control for the callee that blocks transactions to a financial account of the callee.

17. A method of distress assistance, comprising:

detecting an incoming call with a call manager executing on a computing device;

analyzing a conversation between a caller and callee in near real time;

classifying the incoming call as a spam risk based on conversation analysis;

automatically triggering, by the call manager, monitoring of a physical metric of the callee based on the classification of the incoming call as a spam risk;

detecting distress of the callee based on divergence of the physical metric of the callee from a reference physical metric;

selecting an individual associated with the callee in response to detecting the distress, wherein the individual is selected based on determining availability of a set of individuals; and sending a notification of the distress of the callee in near-real time to a selected individual.

18. The method of claim 17, analyzing the conversation further comprising:

monitoring a voice characteristic of the callee;

comparing the voice characteristic of the callee to a voice profile characteristic of the callee;

detecting a distress sentiment based on determining a difference between the voice characteristic and the voice profile characteristic; and identifying distress of the callee based on the distress sentiment.

19. The method of claim 17, further comprising:

pausing the conversation between the caller and the callee; and calling the individual selected to provide assistance to the callee.

20. The method of claim 17, further comprising activating a security control to at least one of mute, interrupt prompt, or forced disconnect of the call in response to classification as a spam risk.

* * * * *